United States Patent [19]
Moore

[11] 3,956,775
[45] May 18, 1976

[54] ROTATOR FOR PROSTHETIC ANKLE JOINT

[76] Inventor: Robert R. Moore, 5401 San Leandro St., Oakland, Calif. 94601

[22] Filed: Feb. 18, 1975

[21] Appl. No.: 550,449

[52] U.S. Cl. .............................................. 3/33; 3/2
[51] Int. Cl.² ...................... A61F 1/04; A61F 1/08
[58] Field of Search ................................... 3/30–35, 3/2, 7, 21

[56] References Cited
UNITED STATES PATENTS

| | | | |
|---|---|---|---|
| 2,475,372 | 7/1949 | Catranis | 3/32 |
| 2,475,373 | 7/1949 | Catranis | 3/32 |
| 3,480,972 | 12/1969 | Prahl | 3/33 |
| 3,842,443 | 10/1974 | Weber | 3/2 |

*Primary Examiner*—Ronald L. Frinks
*Attorney, Agent, or Firm*—Harris Zimmerman

[57] ABSTRACT

A device for joining a prosthetic foot to a prosthetic ankle block with limited, resilient rotation therebetween includes a generally cylindrical adapter or housing secured in the lower end of the ankle block, coaxial with the vertical pivot axis of the foot. An outer spool is secured within the adapter, and an inner spool freely rotates therein on two bearings disposed between the spools and spaced axially there along. A rubber annulus is disposed between the spools intermediate to the bearings, and vulcanized in place to adhere to both spools and form a resilient link therebetween. A pin extends downward from the outer spool to engage a slot in the foot and limit the rotation thereof.

11 Claims, 3 Drawing Figures

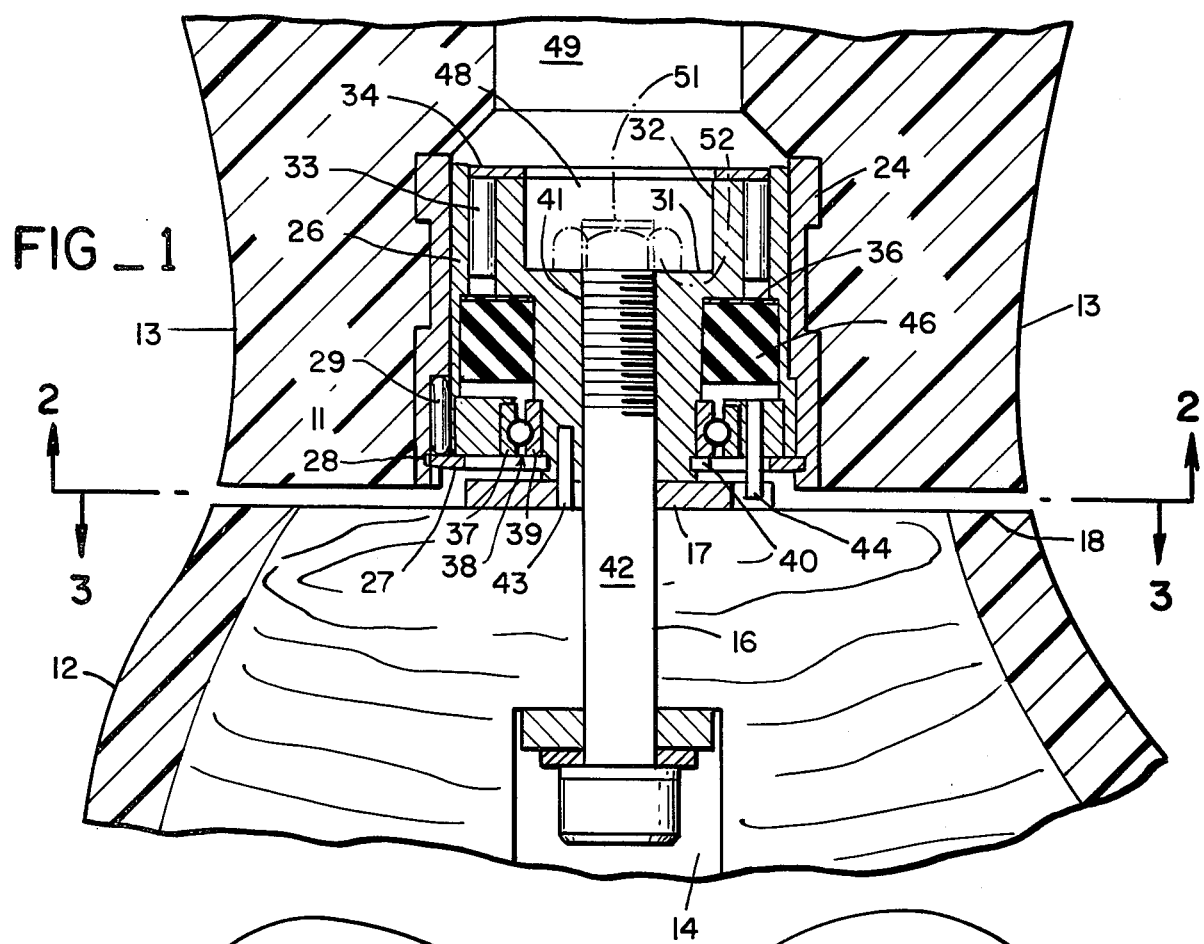
FIG_1
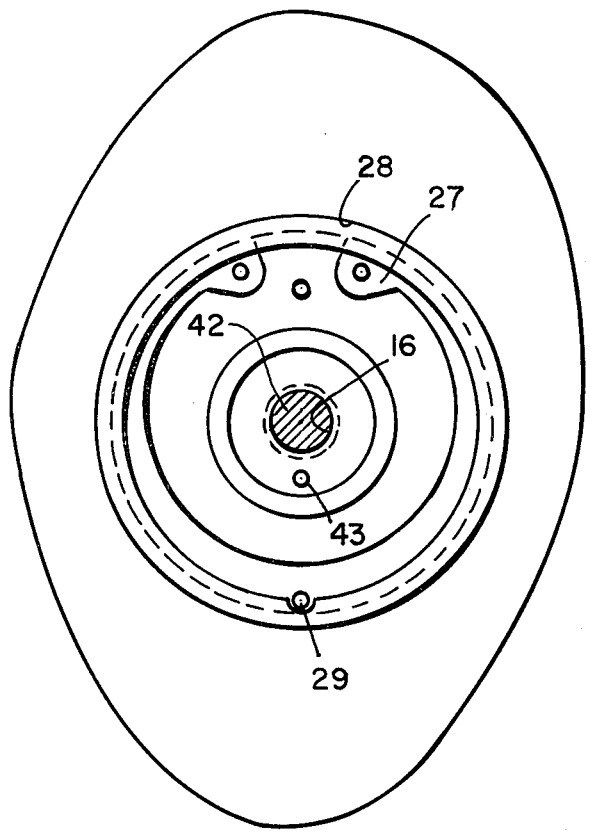
FIG_2
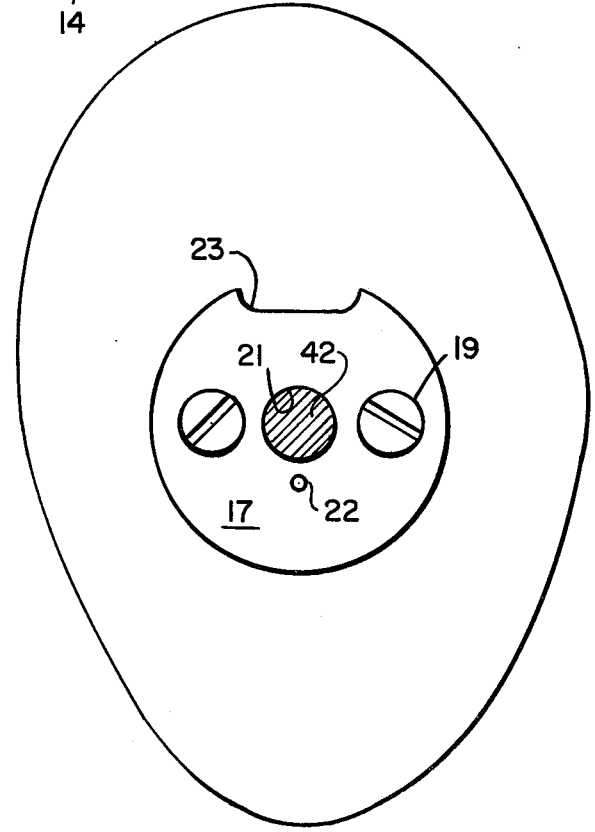
FIG_3

ROTATOR FOR PROSTHETIC ANKLE JOINT

BACKGROUND OF THE INVENTION

An underlying principle of modern prosthetic practice is to produce prosthetic devices which resemble their human counterparts in form and appearance as well as in function and feedom of movement. In the prior art relating to leg and foot prostheses, there are many forms of knee joints, foot joints, and the like. One device that is sadly lacking in the art is an ankle joint which pivots about a vertical axis, allowing the wearer to pivot on the prosthetic leg while the prosthetic foot remains in place. While certain cable rotating devices have been provided, they have not been accepted widely for a number of reasons. Without such a rotatable ankle joint, the wearer must hobble and pivot about the prosthetic leg, or perform other similar awkward maneuvers. In either case the commonly provided rigid ankle joints fail to permit the natural rotary motion and freedom of movement of the human ankle.

SUMMARY OF THE INVENTION

The present invention provides a prosthetic ankle joint which permits limited rotation between the prosthetic foot and leg, and also resiliently biases the foot to return to the normal forward orientation. It includes a vertically disposed hollow cylindrical adapter or housing which is secured in the lower end of the ankle block. An outer spool is secured in the adapter, and an inner spool is rotatably secured in the former by a pair of axially spaced bearings. The inner spool is secured to the foot by an anchor bolt extending therefrom along the pivot axis. A resilient rubber annulus bonded to both the spools and disposed therebetween elastically deforms during rotation of the foot and restores the foot to forward orientation.

Secured to the top face of the foot is a circular plate with a hole through which the anchor bolt extends. A pin extending downwardly from the outer spool engages a narrow notch in the periphery of the plate, to limit the rotation of the foot. A dowel extending from the inner spool and received in a hole in the plate keeps the spool and foot in the proper fixed orientation.

THE DRAWING

FIG. 1 is a cross-sectional side elevation of the rotator assembly of the present invention, installed in an ankle block.

FIG. 2 is a bottom view of the ankle block, taken along line 2—2 of FIG. 1.

FIG. 3 is a top view of the prosthetic foot, taken along line 3—3 of FIG. 1.

DESCRIPTION OF THE PREFERRED EMBODIMENT

The present invention comprises a rotatable joint for pivotably securing a prosthetic foot to a prosthetic leg. As shown in FIG. 1, the rotator 11 secures the prosthetic foot 12 to the ankle block 13 of a prosthetic leg. The foot 12 is provided with a long counterbore 14, from which a hole 16 extends upward. A circular plate 17 is secured to the planar top surface 18 of the foot with wood screws 19 or the like. The plate is provided (see FIG. 3) with a centrally disposed hole 21 aligned with the hole 16, and a smaller dowel hole 22. The plate also includes a notch 23 in the periphery thereof, encompassing an arc of approximately 20°.

The rotator assembly within the ankle block 13 includes a vertically disposed hollow cylindrical adapter or housing 24 fixedly secured in the rigid foam material which comprises the ankle block. Within the adapter bore is disposed an outer spool 26, which is retained therein in the vertical direction by a beveled snap ring 27 which engages an annular groove 28 in the lower end of the adapter bore. A vertically disposed pin 29 received in aligned vertical notches in the outer spool and adapter prevents rotation therebetween.

Disposed within the fixed outer spool is a rotating inner spool 31, which includes an annular shoulder 32 at the upper end thereof. In the annular space between the shoulder and the outer spool are disposed the needles of a needle bearing 33. A bearing shield washer 34 is pressed into the upper end of the outer spool to protect the needle bearing. A washer 36 of Teflon or the like abuts the annular shoulder and seals off the needle bearing from below.

Joined to the lower end of the outer spool is the journal 37 of a ball bearing 38, the inner race 39 being secured to the lower end of the inner spool and retained by retainer ring 40. The ball bearing provides rotational freedom as well as vertical support for the inner spool. The inner spool includes a centrally disposed threaded hole 41 which receives a cap screw 42 extending from the foot 12 through the holes 16 and 21, joining the inner spool to the foot. A vertically disposed dowel pin 43 press fitted in a hole in the inner spool extends downwardly and is received in the hole 22 in the plate 17, thereby fixing the angular orientation of the inner spool with respect to the foot. Another vertically disposed dowel pin 44 extends from the journal 37 downwardly into the notch 23 in the plate 17. This pin limits the rotational motion of the foot about the vertical axis.

The present invention also includes resilient means for restoring the foot to the normal forward orientation. A rubber ring 46 is disposed between the inner and outer spools, abutting the washer 36 and subjacent thereto. The rubber ring is vulcanized in place to bond the vertical sides to the inner and outer spools, elastically joining the two spools together. It may be appreciated that this construction dictates that any rotation of the foot from the forward position (and concomitant rotation of the inner spool) is opposed by the elastic deformation of the ring 46 resulting therefrom. Thus the ring acts to restore the foot to the proper orientation in the absence of torque about the pivot. It should be noted that other resilient means may be employed; however, the rubber ring vulcanized and bonded in place provides the silent operation and durability not found in other means.

The upper annular shoulder 32 defines within its circumference a counterbore 48 which extends coaxially with the hole 41 and communicates therewith. The counterbore is in communication with a cast cylindrical passageway 49 which extends upward to the upper end of the ankle block. In the event that it is desired to secure a single axis foot having a fixed, threaded mounting shaft 51 extending therefrom to the rotator assembly of the present invention, the hole 41 through the inner spool will be provided without threads, so that the shaft 51 (shown in phantom) may extend freely therethrough. A nut 52 (also in phantom) may then be introduced through the passageway 49 and secured to the shaft, joining the single axis foot to the rotator assembly. Thus the present invention has the adaptability to receive either a sach foot which is threadedly secured from below through the foot itself, or a single axis foot which is secured from above with a nut introduced through the ankle block. Due to the dowel pins 43 and 44 which fix and limit the angular orientation of the foot with the ankle block, it is clearly impossible to rotate and threadedly install a single axis foot or the like in a threaded hole in the spool.

Although the present invention is described with reference to its installation in a rigid foam ankle block, it may be appreciated that the invention is sufficiently versatile to be used in other settings. For example, the adaptor may instead be secured in a bored hole within a wooden ankle block by means of adhesives or the like. Similar installation may be made in an ankle block of plastic or the like.

Also, the invention may be placed in an endoskeleton system, or may be fitted into a receptacle emplaced in the prosthetic member to facilitate replacement.

I claim:

1. A device for joining a prosthetic appendage to a prosthetic limb, comprising;
   housing means disposed in said limb,
   a rotating member disposed within said housing means,
   bearing means disposed in said housing means for rotatably supporting said rotating member,
   resilient means joined to said rotating member and said housing means and disposed therebetween,
   anchor means for securing to said rotating member an anchor member extending from the prosthetic appendage,
   said rotating member comprising a cylindrical member having a radial outwardly extending annular shoulder at the upper end thereof.

2. The device of claim 1, wherein said resilient means comprises an elastic rubber ring vulcanized and bonded to said rotating member and said housing means.

3. The device of claim 1, wherein said anchor means comprises a threaded hole extending axially through said rotating member.

4. The device of claim 1, wherein said rotating member includes a hole extending axially therethrough, and a counterbore at said upper end thereof defined by said annular shoulder.

5. The device of claim 4, wherein said anchor means includes a nut received in said counterbore.

6. The device of claim 1, wherein said bearing means includes a needle bearing concentric about said annular shoulder.

7. The device of claim 6, wherein said bearing means includes a ball bearing concentric about the other end of said rotating member.

8. The device of claim 7, wherein said resilient means includes an elastic rubber annulus disposed concentrically between said cylindrical member and said housing means and axially spaced between said needle bearing and said ball bearing.

9. The device of claim 1, further including a plate secured to the top of the appendage.

10. The device of claim 9, including a first pin extending from said housing means in to a notch in said plate to limit rotation of the limb.

11. The device of claim 10, including a second pin secured to said rotating member and said plate to fix the angular relationship therebetween.

* * * * *